(12) United States Patent
Sherman

(10) Patent No.: US 8,056,562 B2
(45) Date of Patent: Nov. 15, 2011

(54) SYSTEM AND METHOD FOR PROVIDING SUPPORT FOR A BREATHING PASSAGE

(75) Inventor: Benjamin Sherman, Milpitas, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 1448 days.

(21) Appl. No.: 11/536,026

(22) Filed: Sep. 28, 2006

(65) Prior Publication Data

US 2008/0078407 A1    Apr. 3, 2008

(51) Int. Cl.
*A62B 7/00* (2006.01)
*A62B 18/08* (2006.01)
*A62B 18/02* (2006.01)
*A61M 16/00* (2006.01)
*A61M 15/00* (2006.01)
*A61F 9/00* (2006.01)
*G02C 7/16* (2006.01)

(52) U.S. Cl. ......... 128/206.24; 128/207.11; 128/207.13; 128/207.17; 128/207.18; 128/204.11; 128/206.11; 128/206.21; 128/200.24; 2/13; 2/15; 351/45

(58) Field of Classification Search ............. 128/207.11, 128/207.13, 207.17, 207.18, 204.11, 206.11, 128/206.21, 200.24; 2/13, 15; 351/45
See application file for complete search history.

(56) References Cited

U.S. PATENT DOCUMENTS

| 4,054,133 A | * | 10/1977 | Myers ....................... 128/204.26 |
| 4,465,067 A | * | 8/1984 | Koch et al. ............... 128/207.18 |
| 5,117,818 A | * | 6/1992 | Palfy ......................... 128/204.11 |
| 6,830,445 B2 | * | 12/2004 | Curti .............................. 425/275 |
| 7,080,645 B2 | | 7/2006 | Genger et al. ........... 128/204.18 |

* cited by examiner

*Primary Examiner* — Patricia Bianco
*Assistant Examiner* — Nihir Patel

(57) ABSTRACT

A system for supporting a breathing passage of a patient may include a cannula and an insertion apparatus. The cannula may be configured to be at least partially inserted into a breathing passage of a patient for supporting the breathing passage during sleep. The cannula may include an insertion end configured to be inserted through a nasal passageway portion of the breathing passage. The insertion apparatus may include a nasal applicator operable to guide the cannula through the nasal applicator and into the nasal passageway, and a support frame coupled to the nasal applicator and configured to be releasably coupled to the patient to position the nasal applicator proximate to the nasal passageway.

23 Claims, 6 Drawing Sheets

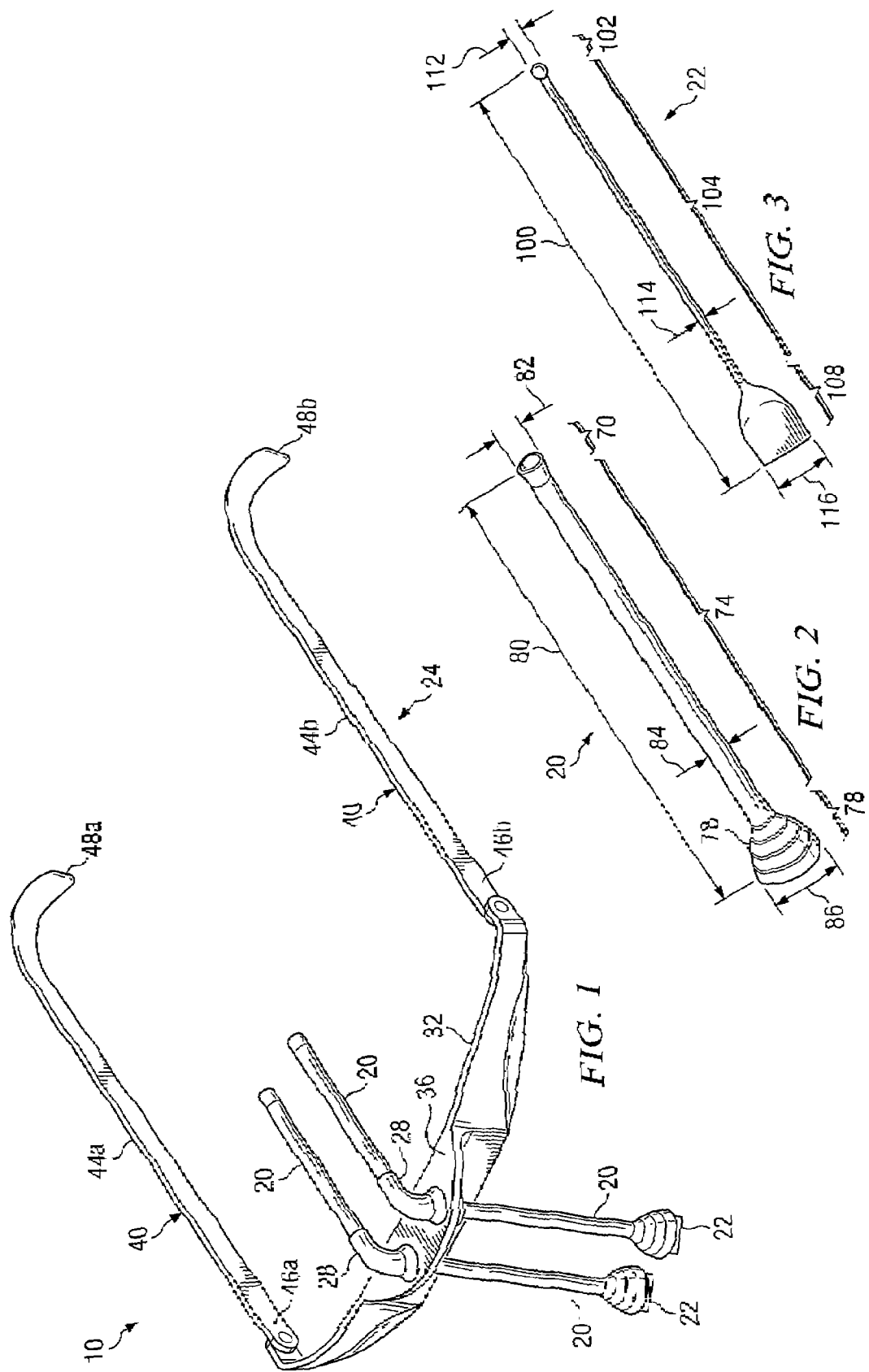

SYSTEM AND METHOD FOR PROVIDING SUPPORT FOR A BREATHING PASSAGE

TECHNICAL FIELD

The present invention relates generally to breathing assistance systems, e.g., a system and method for providing support for a breathing passage.

BACKGROUND

People with untreated sleep apnea may stop breathing during sleep, sometimes hundreds of times during the night and often for a minute or longer. Obstructive sleep apnea (OSA) may be caused by a blockage of the airway, typically when soft tissue at the rear of the throat collapses and closes during sleep.

Treatment of sleep apnea attempts to restore regular nighttime breathing. According to one known treatment, continuous positive airway pressure (CPAP) is used to maintain breathing. In this treatment, the patient may wear a mask over his nose during sleep. The mask delivers air into the throat to increase the airway pressure in order to keep the throat open during sleep. According to another known treatment, the patient wears an oral appliance during sleep. The oral appliance adjusts the lower jaw and tongue to keep the throat open during sleep. According to yet another known treatment, surgery may be used to correct airways. Such surgery may be performed to remove tissue that may block the airway, for example, the tonsils, adenoids, or uvula.

SUMMARY

In accordance with one embodiment of the present disclosure, a system for supporting a breathing passage of a patient may include a cannula and an insertion apparatus. The cannula may be configured to be at least partially inserted into a breathing passage of a patient for supporting the breathing passage during sleep. The cannula may include an insertion end configured to be inserted through a nasal passageway portion of the breathing passage. The insertion apparatus may include a nasal applicator operable to guide the cannula through the nasal applicator and into the nasal passageway, and a support frame coupled to the nasal applicator and configured to be releasably coupled to the patient to position the nasal applicator proximate to the nasal passageway.

In accordance with another embodiment of the present disclosure, an insertion apparatus for use with a system for supporting a patient's breathing passage may include a nasal applicator and a support frame coupled to the nasal applicator. The nasal applicator may be operable to guide an insertion end of a cannula into a nasal passageway of a patient's breathing passage to at least partially insert the cannula into the breathing passage to support the breathing passage during sleep. The support frame may be configured to be releasably coupled to the patient to position the nasal applicator proximate to the nasal passageway.

In accordance with another embodiment of the present disclosure, a cannula for supporting a breathing passage of a patient may include an elongated portion, an insertion end, and a restriction end. The elongated portion may be configured to support a breathing passage of the patient during sleep. The insertion end may be configured to be inserted through a nasal applicator of an insertion apparatus and through a nasal passageway of a breathing passage of the patient such that the elongated portion is at least partially disposed within the breathing passage. The restriction end may have a restriction end diameter greater than a diameter of a nasal vestibule of the nasal passageway to prevent the cannula from passing completely through the nasal passageway.

In accordance with another embodiment of the present disclosure, a method for inserting a cannula for supporting a patient's breathing passage may include removably coupling a support frame of an insertion apparatus to a patient to position a nasal applicator proximate to a nasal passageway of a breathing passage of the patient, and guiding an insertion end of a cannula through the nasal applicator and through the nasal passageway such that the cannula is at least partially inserted into the breathing passage for supporting the breathing passage during sleep.

In accordance with another embodiment of the present disclosure, a nasal applicator for use with a system for supporting a patient's breathing passage is provided. The nasal applicator may be configured to be removably coupled to a support frame configured to position the nasal applicator proximate to a nasal passageway of a patient's breathing passage. The nasal applicator may further be configured to guide a cannula into the nasal passageway for at least partially inserting the cannula into the breathing passage for supporting the breathing passage during sleep.

In accordance with another embodiment of the present disclosure, a system for supporting a breathing passage of a patient may include support means for supporting the breathing passage and insertion means for inserting the support means into the breathing passage. The support means may include an insertion end configured to be inserted through a nasal passageway of the breathing passage to at least partially insert the support means into the breathing passage. The insertion means may include nasal application means operable to guide the support means through the nasal application means and into the nasal passageway, and patient interfacing means for positioning the nasal application means proximate to the nasal passageway. The patient interfacing means may be configured to be releasably coupled to the patient to position the nasal applicator proximate to the nasal passageway.

BRIEF DESCRIPTION OF THE DRAWINGS

FIG. 1 illustrates an example system for inserting a cannula into a patient's breathing passage for supporting the breathing passage, according to one embodiment of the disclosure;

FIG. 2 illustrates an example cannula that may be used with the system of FIG. 1, according to one embodiment of the disclosure;

FIG. 3 illustrates an example guiding shaft that may be used with the system of FIG. 1, according to one embodiment of the disclosure;

DETAILED DESCRIPTION OF THE DRAWING

Figure 4A:
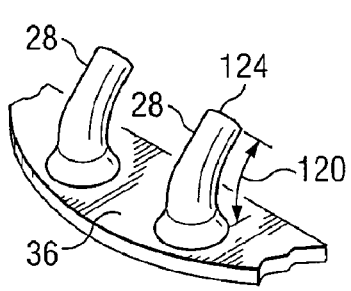
FIG. 4A illustrates example nasal applicators that may be used with the system of FIG. 1, according to one embodiment of the disclosure.

Selected embodiments of the disclosure may be understood by reference, in part, to FIGS. 1 through 6C, wherein like numbers refer to same and like parts. The present disclosure relates generally to providing support for a patient's breathing passage.

In accordance with one embodiment of the present disclosure, a system for providing support for a patient's breathing passage (e.g., by resisting collapsing or other obstructions of the breathing passage during sleep) may include one or more cannulas and an insertion apparatus. The insertion apparatus may include a support frame and one or more nasal applicators coupled to the support frame. The support frame may be configured to be releasably coupled to the patient to position the one or more nasal applicators proximate to the one or more nasal passageways. Each nasal applicator may be configured to guide an insertion end of a cannula through the nasal applicator and into a nasal passageway. The cannula may be advanced through the nasal passageway until the cannula is positioned in the breathing passage as desired for resisting collapsing or other obstructions of the breathing passage during sleep. For example, in some embodiments, the cannula may resist or prevent collapses of the soft palate and/or the tongue that would obstruct the breathing passage. In some embodiments, each cannula may include a restriction end to prevent the cannulas from being completely advanced through the nasal passageways.

FIG. 1 illustrates an example system 10 for inserting a cannula 20 into a breathing passage for supporting the breathing passage, according to one embodiment of the disclosure. According to one embodiment, one or two cannulas 20 may be inserted into the patient's nasal passageways in order to support the patient's breathing passage while the patient is sleeping. Thus, system 10 may be configured to reduce or prevent sleep apnea.

As used herein, the term "patient" may refer to any person or animal that may use system 10, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

A patient's respiratory system includes various structures for allowing the patient to breath, including the nose/nasal structure, the pharynx (throat), the larynx (voice box), the trachea (windpipe), bronchi, and the lungs. The nasal structure may include one or more nasal vestibules, one or more nasal passageways, and a nasal cavity. Typically, a human has two nasal vestibules, two nasal passageways, and one nasal cavity. A nasal vestibule serves as the opening, where air, $CO_2$, and/or other gasses enter and exit the patient. Each nasal vestibule leads to a nasal passageway, which leads to the nasal cavity. The pharynx passes air from the nasal cavity to the trachea, and the epiglottis guards the entrance to the trachea. When a person swallows, the epiglottis closes to allow the swallowed matter to pass through to the esophagus, which leads from the pharynx to the stomach.

As used herein, the term "breathing passage" may refer to any passageway defined by the respiratory system. For example, the breathing passage may include all or portions of the nasal structure, the pharynx, and/or the trachea.

As used herein, to "support the breathing passage" means to resist or prevent the breathing passage from collapsing or otherwise becoming obstructed, e.g., as experienced by patient's suffering from sleep apnea. Thus, each cannula 20 may support a patient's breathing passage by resisting or preventing the breathing passage from collapsing or otherwise becoming obstructed (e.g., during sleep or otherwise). For example, in some embodiments, each cannula 20 may resist or prevent collapses of the soft palate and/or the tongue that would obstruct the breathing passage.

According to one embodiment, a user may use system 10 to insert cannula 20 into a patient. As used herein, the term "user" may refer to any person who can operate system 10 to insert cannula 20 into a patient. In some cases, the user may be the patient. That is, the patient may use system 10 to insert cannula 20 into himself or herself. In other cases, the user may be distinct from the patient. That is, the user may use system 10 to insert cannula 20 into the patient.

According to the illustrated embodiment, system 10 may include one or more cannulas 20, one or more guiding shafts 22, and an insertion apparatus 24. A cannula 20 may represent a tube that can be inserted into a body cavity or duct. For example, cannula 20 may be inserted into the breathing passage through a nasal passageway. Cannula 20 is described in more detail with reference to FIG. 2. A guiding shaft 22 may be used to guide a cannula 20 into the breathing passage. Guiding shaft 22 may comprise a solid or tubular shaft that may be disposed within cannula 20 to guide and/or support cannula 20 as cannula 20 is inserted into the breathing passage. Guiding shaft 22 may be removed from cannula 20 after cannula 20 is inserted into the breathing passage. An example guiding shaft 22 is described in more detail below with reference to FIG. 3.

According to one embodiment, insertion apparatus 24 may be used to insert one or more cannulas 20 into a patient's breathing passage (e.g., via one or both nasal passageways). Insertion apparatus 24 may comprise one or more components that may be coupled in any suitable manner. According to the illustrated embodiment, insertion apparatus 24 may include one or more nasal applicators 28 and a support frame 32. In this embodiment, insertion apparatus 24 includes two nasal applicators 28. In other embodiments, insertion apparatus 24 may include a single nasal applicator 28. Each nasal applicator 28 may be used to guide a cannula 20 into a nasal passageway. For example, a user may place a leading end of cannula 20 within nasal applicator 28 and push cannula 20 through nasal applicator 28. Nasal applicator 28 may guide the leading end of cannula 20 through the nasal passageway as the user advances cannula 20. A trailing end of cannula 20 may be passed through nasal applicator 28 to allow for removal of insertion apparatus 24. Nasal applicator 28 is described in more detail below with reference to FIGS. 4A and 4B. According to one embodiment, insertion apparatus 24 may include a pair of nasal applicators 28 that are inserted into the nasal vestibules.

Support frame 32 may be configured to position nasal applicators 28 proximate to the nasal passageways to allow for insertion of cannulas 20 into the nasal passageways. In some embodiments, support frame 32 may be releasably coupled to the patient for the insertion of cannulas 20. According to the illustrated embodiment, support frame 32 may include a nasal portion 36 and one or more coupling portions 40. Nasal portion 36 may support nasal applicators 28.

In some embodiments, nasal applicators 28 may be permanently coupled to nasal portion 36. In such embodiments, nasal applicators 28 are removed from the face along with the remainder of insertion apparatus 24 once cannulas 20 are inserted into the breathing passage. Thus, nasal applicators 28 and the restriction end 78 of each cannula 20 may be configured to allow restriction end 78 of each cannula 20 to pass completely through a nasal applicator 28 in order to remove insertion apparatus 24 from the face. In some embodiments, restriction end 78 of cannula 20 is configured such that it may be flexed, folded, squeezed, or otherwise deformed in order to pass through nasal applicator 28. In other embodiments, restriction end 78 and the opening extending through nasal applicator 28 may be sized such that restriction end 78 may pass through nasal applicator 28 without deforming restriction end 78 or nasal applicator 28.

In other embodiments, nasal applicators 28 may be removably coupled to nasal portion 36. In such embodiments, nasal applicators 28 may remain in place (i.e., at least partially disposed within the nose) along with cannulas 20 once cannulas 20 are inserted into the breathing passage. Nasal applicators 28 may then be removed along with cannulas 20 when cannulas 20 are removed (e.g., after the patient awakens). In addition or alternatively, nasal applicators 28 may be removably coupled to nasal portion 36 such that nasal applicators 28 may be cleaned and/or replaced.

Nasal applicators 28 may be removably coupled to nasal portion 36 in any suitable manner. For example, nasal applicators 28 may be coupled to nasal portion 36 using clips or other mechanical fasteners, or nasal applicators 28 may include flanges or other deformable members that may be manipulated in order to couple nasal applicators 28 with nasal portion 36.

Coupling portions 40 may couple insertion apparatus 24 to the patient to position nasal applicators 28 proximate to the patient's nasal passageways. In the illustrated embodiment, coupling portions 40 comprise arms 44. Each arm 44 may include a coupling end 46 and an ear piece 48. Coupling end 46 may be coupled to nasal portion 36. Ear piece 48 may fit over the ear of the patient. The ear may support arm 44, allowing insertion apparatus 24 to be releasably coupled to the patient. Coupling portions 40 may couple nasal portion 36 to the patient in any other suitable manner. For example, coupling portions 40 may comprise a band (for example, an elastic band) that may fit around the head of the patient. As another example, coupling portions 40 may comprise a headgear that fits over the head of the patient. As yet another example, coupling portions 40 may comprise an adhesive that may be releasably coupled to the patient.

In some embodiments, insertion apparatus 24 and cannulas 20 may be designed such that insertion apparatus 24 may be removed after cannulas 20 have been inserted into the patient's breathing passage. For example, cannulas 20 may be shaped to pass through nasal applicators 28. In other embodiments, insertion apparatus 24 may be configured to be worn after cannulas 20 have been inserted (e.g., insertion apparatus 24 may be configured to be worn as the patient sleeps).

The components of insertion apparatus 24 may be coupled together in any suitable manner. As an example, certain components may mechanically coupled, e.g., using one or more of any of the following: a bolt, a rivet, a screw, a nail, a pin, a cable, a clamp, a lock, a hook, other mechanical fastener, or any combination of any of the preceding. As another example, certain components may chemically coupled, e.g., using an adhesive and/or solder. As another example, certain components may magnetically coupled.

Modifications, additions, or omissions may be made to system 10 without departing from the scope of the invention. The components of system 10 may be integrated or separated according to particular needs. For example, certain components of insertion apparatus 24 may be coupled together and then decoupled. Moreover, the functionality provided by system 10 may be performed by more, fewer, or other components. For example, the functions of nasal portion 36 and coupling portions 40 may be performed by a single component, or the functions of nasal portion 36 may be performed by more than one component.

FIG. 2 illustrates an example cannula 20 that may be used with system 10 of FIG. 1, according to one embodiment of the disclosure. Cannula 20 may be formed from any suitable material or materials. According to one embodiment, cannula 20 may be formed from one or more deformable materials that sufficiently bend to allow cannula 20 to fit into the breathing passage, but that sufficiently maintain shape to allow cannula 20 to be inserted into the breathing passage. Examples of such deformable material include plastic, silicon, vinyl, other deformable material, or any combination of any of such materials.

In some embodiments, at least an outer surface of cannula 20 may be formed from, or coated with, one or more materials that may increase the comfort of cannula 20 being inserted in the breathing passage. For example, an outer surface of cannula 20 may be formed from a relatively low-friction material. As another example, an outer surface of cannula 20 may be coated with a lubricating or low-friction gel or other coating before being inserted into the breathing passage. As another example, an outer surface of cannula 20 may be coated with a numbing, anesthetizing, or desensitizing gel or other coating before being inserted into the breathing passage.

Cannula 20 may comprise a tube having any suitable length 80, cross-section, and diameter. According to some embodiments, length 80 may be sufficient to support portions of the breathing passage that may collapse or otherwise become obstructed during sleep or otherwise. For example, length 80 may be configured such that cannula 20 extends from the nasal vestibule to an area at or just beyond the back of the tongue. As another example, cannula 20 may extend to an area just before the epiglottis. As another example, cannula 20 may extend just past the epiglottis. As another example, cannula 20 may extend at least partially into the trachea. The distance that cannula 20 extends into the breathing passage depends on the physical geometry of the particular patient 12. Thus, cannulas 20 of different lengths 80 may be manufactured such that particular cannulas 20 may be selected for use with particular patients 12.

Cannula 20 may have any suitable cross-section sufficient to support the breathing passage. For example, cannula 20 may have a rounded, for example, circular, elliptical, or otherwise rounded cross-section.

According to the illustrated embodiment, cannula 20 may have an insertion end 70, an elongated portion 74, and a restriction end 78. Insertion end 70 may have any suitable shape that facilitates insertion of cannula 20 into a nasal passageway. According to one embodiment, insertion end 70 may have a rounded shape. Elongated portion 74 may be shaped or configured for communicating gas through the patient's breathing passage. Restriction end 78 may be shaped or configured to prevent the entire cannula 20 from entering the breathing passage (e.g., to prevent the entire cannula 20 from passing through the nasal passageway).

Insertion end 70 may have any suitable diameter 82, elongated portion 74 may have any suitable diameter 84, and restriction end 78 may have any suitable diameter 86. Diameters 82, 84, and 86 may refer to diameters of cannula 20 in its natural shape or cannula 20 as deformed, for example, by the breathing passage. Diameters 82, 84, and 86 may also vary along cannula 20. According to one embodiment, diameters 82 and 84 may allow cannula 20 to pass through the breathing passage of the patient. For example, diameters 82 and 84 may be approximately equivalent to or less than the narrowest portion of the breathing passage. According to one embodiment, diameter 84 of elongated portion 74 may be less than diameter 82 of insertion end 70. Further, diameter 86 of restriction end 78 may prevent the entire cannula 20 from entering the breathing passage. For example, diameter 86 of restriction end 78 may be greater than the diameter of the nasal vestibule of the nasal passageway such that restriction end 78 is restricted from passing through the nasal vestibule. Thus, in some embodiments, at least a portion of restriction end 78 may remain outside of the patient's nose after cannula 20 is inserted.

FIG. 3 illustrates an example guiding shaft 22 that may be used with system 10 of FIG. 1, according to one embodiment of the disclosure. Guiding shaft 22 may be shaped or configured to be disposed within cannula 20 for guiding or directing insertion end 70 of cannula 20 along the breathing passage. According to one embodiment, guiding shaft 22 may be more rigid than cannula 20 in order to facilitate the guidance of insertion end 70.

Guiding shaft 22 may comprise any suitable material. According to one embodiment, guiding shaft 22 may comprise one or more deformable materials that sufficiently bend to allow guiding shaft 22 to fit into the breathing passage, but that sufficiently maintain shape to allow guiding shaft 22 to be inserted into the breathing passage. Examples of deformable material include plastic, silicon, vinyl, other deformable material, or any combination of such materials.

Guiding shaft 22 may comprise a substantially hollow tube or a substantially solid shaft having any suitable length 100, cross-section, and diameter. According to one embodiment, length 100 may be substantially equivalent to length 80. According to the illustrated embodiment, guiding shaft 22 has a guiding end 102, an elongated portion 104, and a restriction end 108. Guiding end 102 may have a shape that allows for insertion of guiding shaft 22 into the nasal passageway of the patient. According to one embodiment, guiding end 102 may have a rounded shape. Elongated portion 104 may have any suitable cross-section sufficient to guide or direct cannula 20. For example, cannula 20 may have a rounded (e.g., circular, oval, elliptical, or otherwise rounded) cross-section. Like restriction end 78 of cannula 20, restriction end 108 of guiding shaft 22 may be shaped or configured to prevent the entire guiding shaft 22 from entering the breathing passage (e.g., to prevent the entire guiding shaft 22 from passing through the nasal passageway).

Guiding end 102 may have any suitable diameter 112, elongated portion 104 may have any suitable diameter 114, and restriction end 108 may have any suitable diameter 116. Diameters 112, 114, and 116 may vary along guiding shaft 22. According to one embodiment, diameters 112 and 114 may allow guiding shaft 22 to fit within cannula 20. For example, diameters 112, 114, and 116 may be slightly less than diameters 82, 84, and 86 of cannula 20. Restriction end 108 may have a diameter 116 that prevents guiding shaft 22 from passing through cannula 20. Restriction end 108 may further be shaped or configured such that a portion of restriction end 108 extends beyond restriction end 78 of cannula 20 such that guiding shaft 22 may be removed from cannula 20 (e.g., after cannula 20 is inserted in the patient's breathing passage).

FIG. 4A illustrates example nasal applicators 28 that may be used with system 10 of FIG. 1, according to one embodiment of the disclosure. Nasal applicator 28 may be shaped or configured to guide cannulas 20 towards and into the breathing passage. According to the illustrated embodiment, nasal applicator 28 includes a curve configured to guide cannula 20 towards and into a nasal passageway. Nasal applicator 28 may fit against or within the entrance of the nasal passageway. For example, according to the illustrated embodiment, a nasal end 124 of nasal applicator 28 may have a substantially conical shape configured to fit within a nasal vestibule. Nasal applicator 28 may have any suitable length 120 to allow nasal apparatus 28 to guide cannula 20 into the nasal passageway.

Figure 4B:
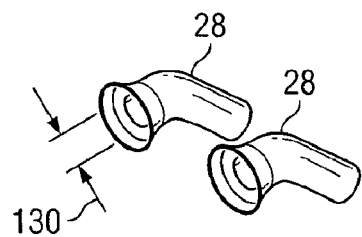
FIG. 4B illustrates another view of the nasal applicators of FIG. 4A, according to one embodiment of the disclosure.

FIG. 4B illustrates another view of example nasal applicators 28 of FIG. 4A. Nasal applicator 28 may have any suitable diameter 130. According to one embodiment, diameter 130 may be selected to allow cannula 20 to pass through nasal applicator 28. For example, the smallest diameter 130 of nasal applicator 28 may be equal to or greater than the largest diameter 86 of cannula 20. Nasal applicator 28 may have any suitable cross-section. For example, nasal applicator 28 may have a rounded, for example, circular, elliptical, or otherwise rounded cross-section.

Figure 5A:
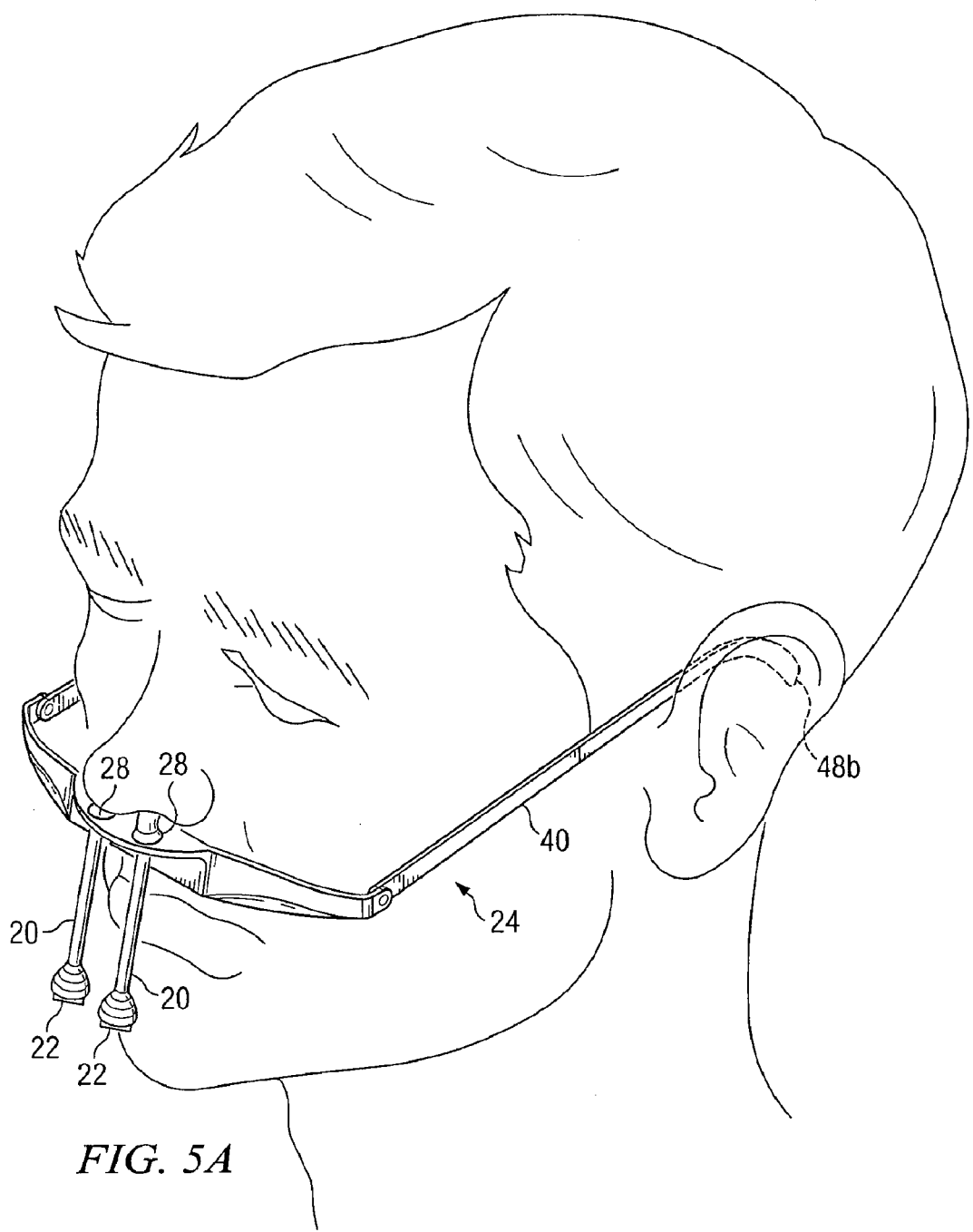
FIG. 5A illustrates a perspective view of the insertion of cannulas into a patient's breathing passage using the insertion apparatus of FIG. 1, according to one embodiment of the disclosure.

FIG. 5A illustrates a perspective view of the insertion of cannulas 20 into a patient's breathing passage using insertion apparatus 24, according to one embodiment of the disclosure. According to the illustrated embodiment, coupling portions 40 may be coupled to the patient's ears, e.g., similar to a pair of eyeglasses. Nasal portion 36 may be positioned under the nose, and nasal applicators 28 may be at least partially disposed within the nasal vestibules. Guiding shafts 22 may be at least partially disposed within cannulas 20, and cannulas 20 may be at least partially disposed within nasal applicators 28. Cannulas 20 and guiding shafts 22 may then be advanced though nasal applicators 28 and into the breathing passage as desired.

Figure 5B:
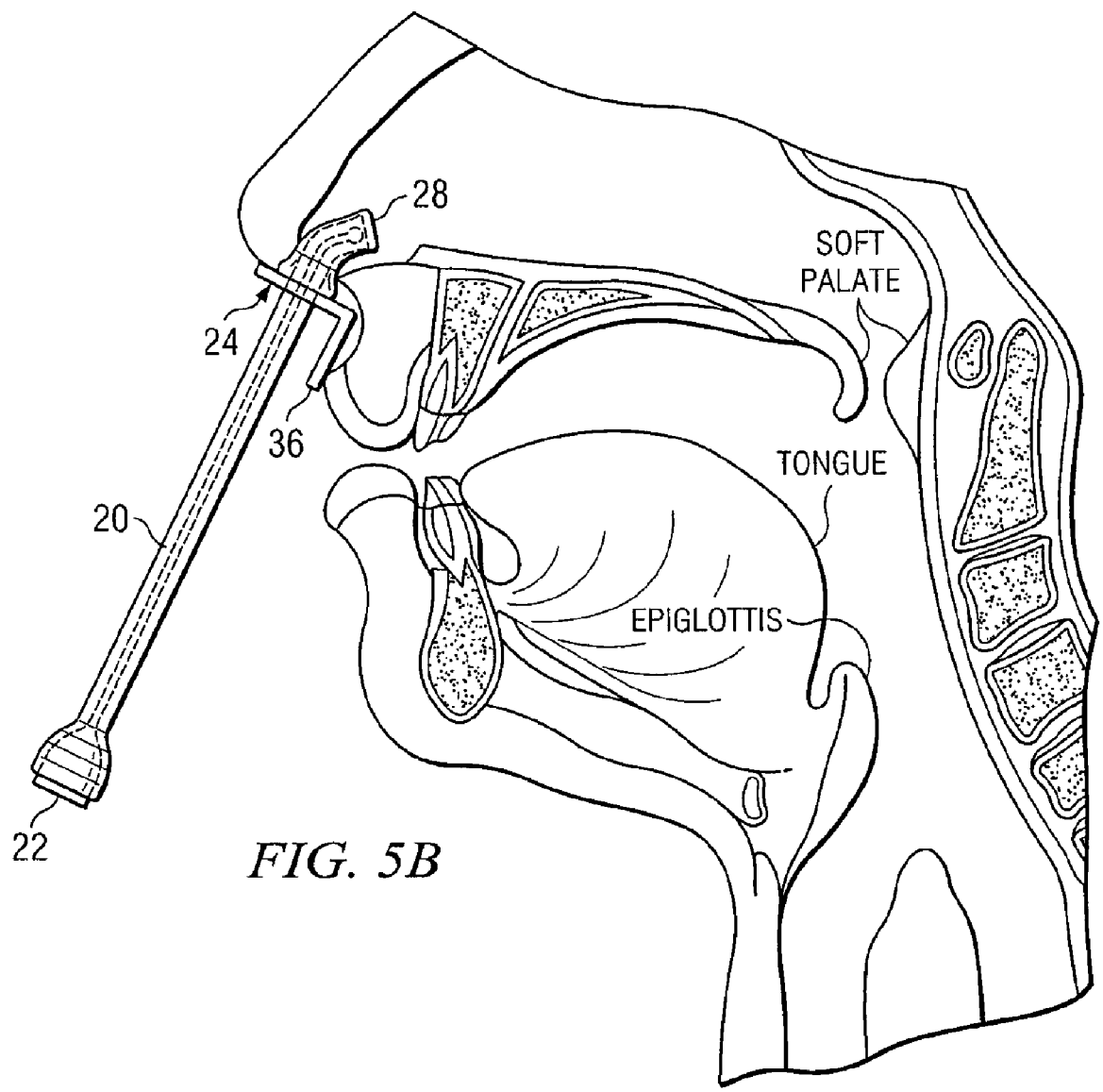
FIG. 5B illustrates a cross-sectional view of the insertion of cannulas into the breathing passage, according to one embodiment of the disclosure.

FIG. 5B illustrates a cross-sectional view of the insertion of cannulas 20 into the patient's breathing passage, according to one embodiment of the disclosure. According to the illustrated embodiment, guiding shaft 22 may be at least partially disposed within cannula 20, and cannula 20 may be advanced through nasal applicator 28. Nasal applicator 28 may direct cannula 20 and guiding shaft 22 into the nasal passageway.

Figure 6A:
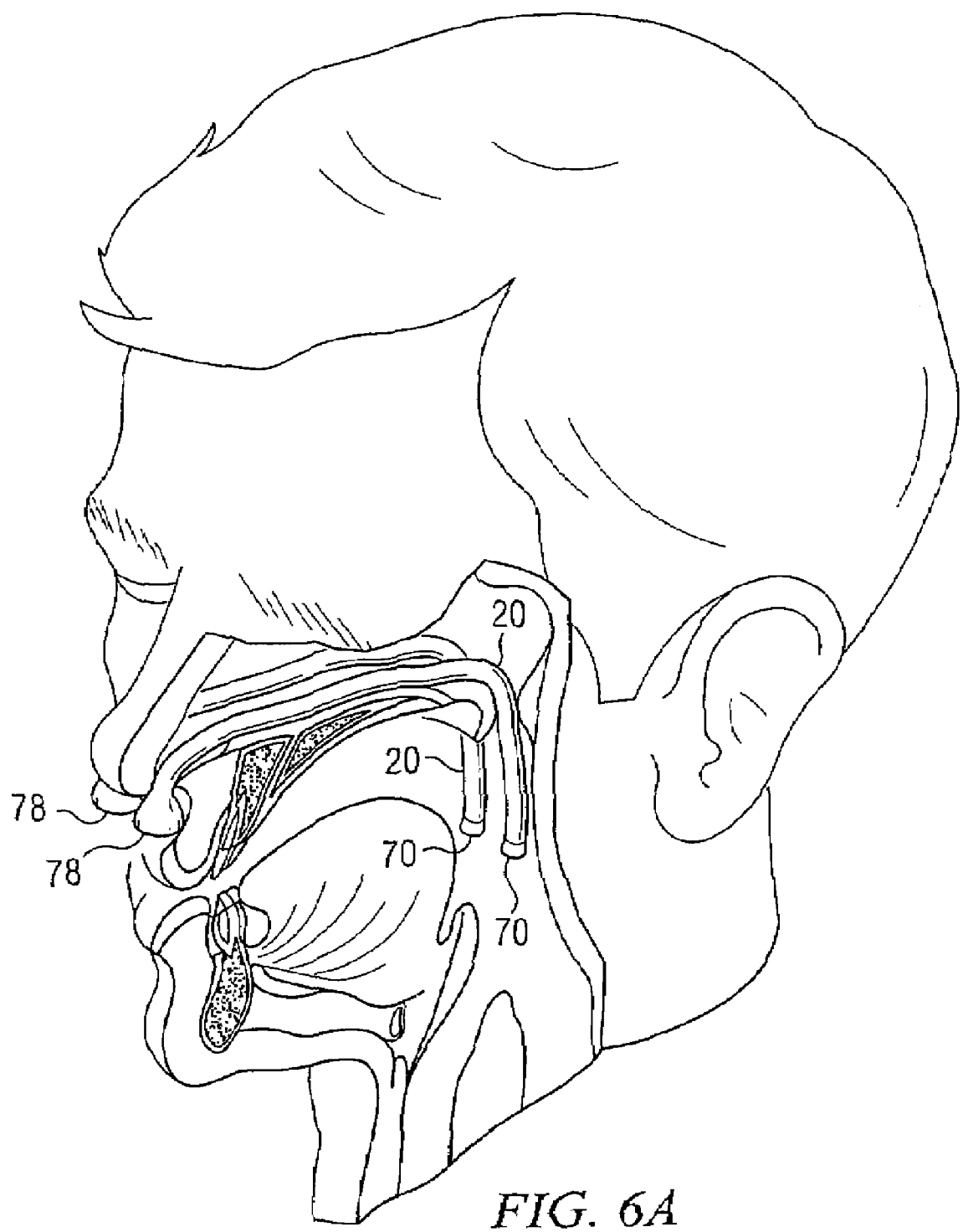
FIGS. 6A and 6B illustrate a perspective view and a cross-sectional view, respectively, of cannulas inserted into the breathing passage of a patient, according to an embodiment in which nasal applicators are removed from the cannulas after insertion of the cannulas.
Figure 6B:
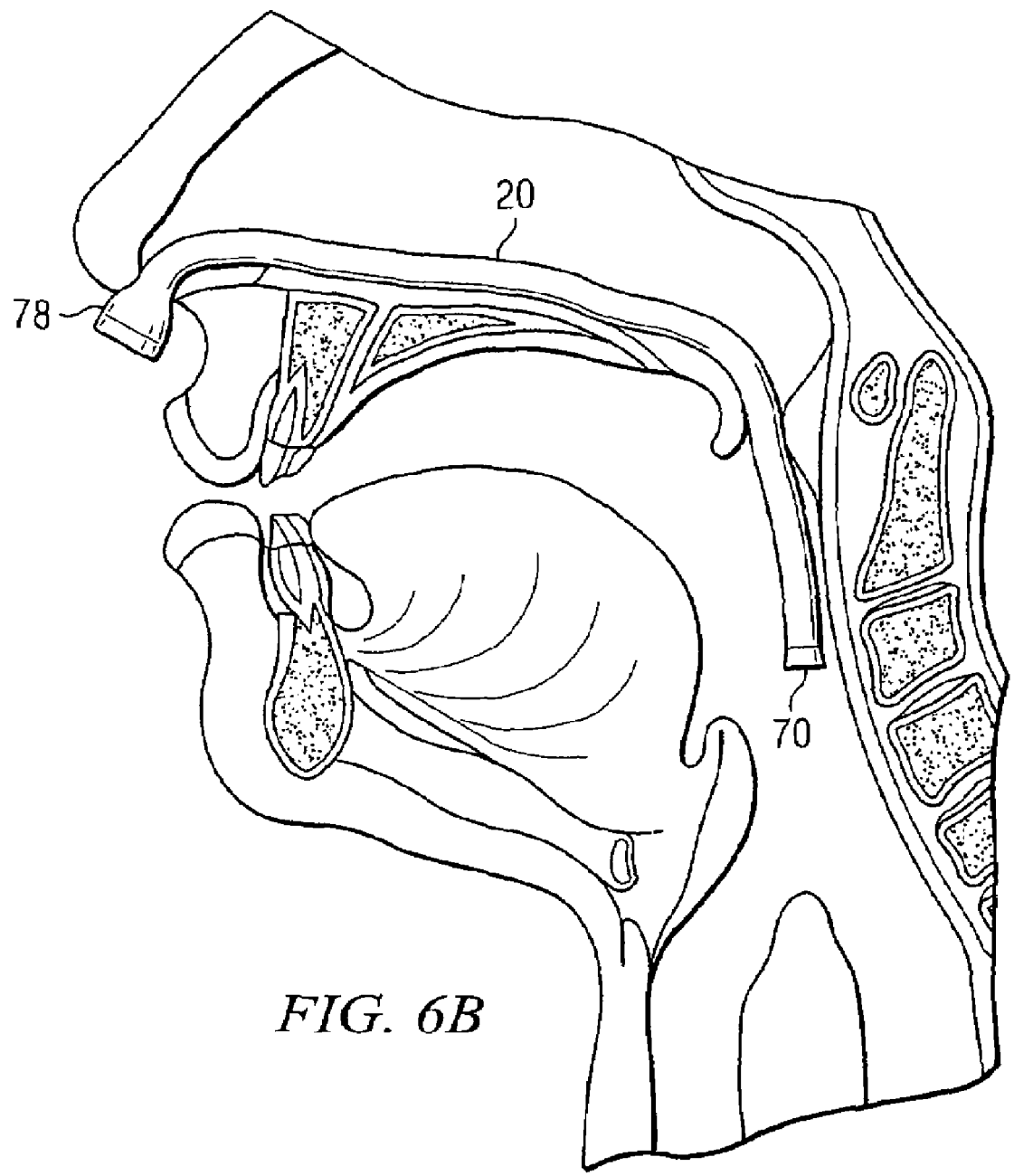

FIGS. 6A and 6B illustrate a perspective view and a cross-sectional view, respectively, of cannulas 20 inserted into the breathing passage of a patient, according to an embodiment in which nasal applicators 28 (along with the remainder of insertion apparatus 24) are removed from cannulas 20 after insertion of cannulas 20. Cannulas 20 may be inserted into the breathing passage via the nasal vestibules. Restriction end 78 of each cannula 20 may remain at least partially outside of or within the nasal vestibule of the patient to prevent the entire cannula 20 from advancing into the breathing passage.

Insertion end 70 of each cannula 20 may extend any suitable distance into the breathing passage, depending, e.g., on the length 80 of the cannula 20 and/or the physical geometry of the particular patient 12. For example, as discussed above, insertion end 70 of each cannula 20 may extend to area at or just beyond the back of the tongue, may extend to an area just before the epiglottis, may extend just past the epiglottis, or may extend at least partially into the trachea.

In this embodiment, nasal applicators 28 are removed from the face along with the remainder of insertion apparatus 24 once cannulas 20 are inserted into the breathing passage. For example, restriction end 78 of each cannula 20 may pass completely through a respective nasal applicator 28 in order to move insertion apparatus 24 away from the face. As discussed above, in some embodiments, restriction end 78 of each cannula 20 may be flexed, folded, squeezed, or otherwise deformed in order to pass through nasal applicator 28. In some embodiments, restriction end 78 and the opening defined by nasal applicator 28 may be sized such that restriction end 78 may pass through nasal applicator 28 without deforming restriction end 78 or nasal applicator 28.

Figure 6C:
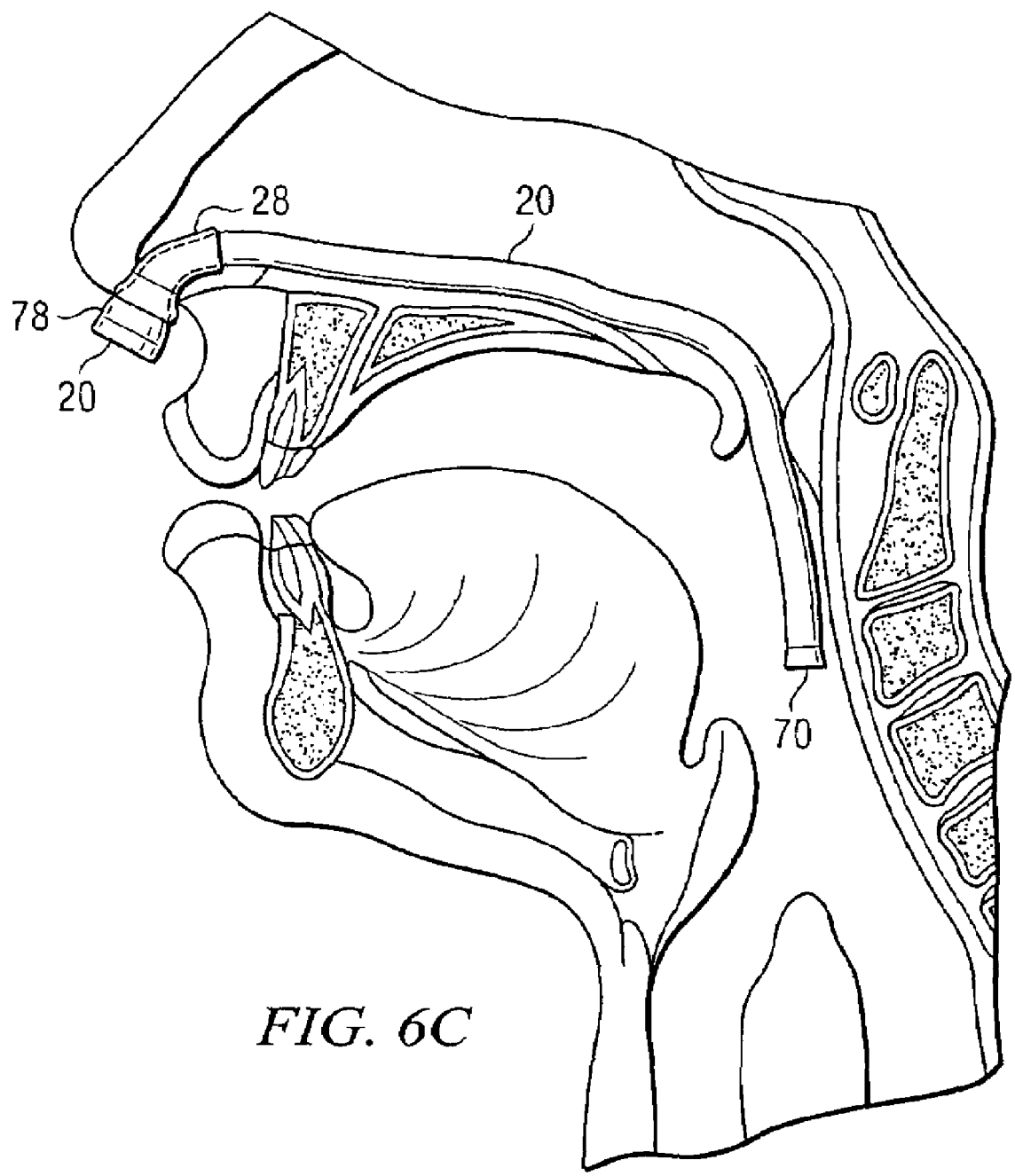
FIG. 6C illustrates a cross-sectional view of cannulas inserted into the breathing passage of a patient, according to an embodiment in which nasal applicators remain attached to the cannulas after insertion of the cannulas.

FIG. 6C illustrates a cross-sectional view of cannulas 20 inserted into the breathing passage of a patient, according to an embodiment in which nasal applicators 28 remain in place along with cannulas 20 once cannulas 20 are inserted into the breathing passage.

While the invention may be susceptible to various modifications and alternative forms, specific embodiments have been shown by way of example in the drawings and have been described in detail herein. It should be understood, however, that the invention is not intended to be limited to the particular forms disclosed. Rather, the invention is to cover all modifications, equivalents, and alternatives falling within the spirit and scope of the invention as defined by the following appended claims.

What is claimed is:

1. A system for supporting a breathing passage of a patient, comprising:
    a cannula configured to be at least partially inserted into a breathing passage of a patient, the cannula comprising:
        an insertion end configured to be inserted through a nasal passageway of the breathing passage;
        a restriction end having a restriction end diameter, the restriction end diameter greater than a diameter of a nasal vestibule of the nasal passageway to prevent the cannula from passing completely through the nasal passageway; and
        a cross-section sufficient to support the breathing passage during sleep; and
    an insertion apparatus including:
        a nasal applicator operable to guide the cannula through the nasal applicator and into the nasal passageway, wherein the nasal applicator fits within the nasal passageway and includes a curve configured to guide the cannula within the nasal passageway; and
        a support frame coupled to the nasal applicator, the support frame configured to be releasably coupled to the patient to position the nasal applicator proximate to the nasal passageway.

2. A system according to claim 1, further comprising a guiding shaft configured to be disposed within the cannula for directing the insertion end of the cannula through the nasal passageway.

3. A system according to claim 1, wherein the cannula has a length approximately equivalent to a distance between a nasal vestibule of the nasal passageway and an epiglottis of the patient.

4. A system according to claim 1, wherein the cannula is formed from one or more deformable materials.

5. A system according to claim 1, where the support frame includes:
    a nasal portion operable to support the nasal applicator; and
    one or more coupling portions operable to removably couple the nasal portion to the patient to position the nasal applicator proximate to the nasal passageways.

6. A system according to claim 1, further comprising:
    a second cannula configured to be at least partially inserted into the breathing passage of the patient for supporting the breathing passage during sleep, the second cannula having an insertion end configured to be inserted through a second nasal passageway of the breathing passage; and
    wherein the insertion apparatus includes a second nasal applicator operable to guide the second cannula through the second nasal applicator and into the second nasal passageway, the second nasal applicator coupled to the support frame.

7. An insertion apparatus for use with a system for supporting a patient's breathing passage, comprising:
    a nasal applicator operable to guide an insertion end of a cannula into a nasal passageway of a patient's breathing passage to at least partially insert the cannula into the breathing passage, the cannula having a cross-section sufficient to support the breathing passage during sleep, wherein the nasal applicator fits within the nasal passageway and includes a curve configured to guide the cannula within the nasal passageway; and
    a support frame coupled to the nasal applicator, the support frame configured to be releasably coupled to the patient to position the nasal applicator proximate to the nasal passageway, wherein the support frame includes:
        a nasal portion operable to support the nasal applicator; and
        one or more coupling portions operable to removably couple the nasal portion to the patient to position the nasal applicator proximate to the nasal passageway.

8. An apparatus according to claim 7, further comprising a guiding shaft configured to be disposed within the cannula for directing the insertion end of the cannula through the nasal passageway.

9. An apparatus according to claim 7, wherein the cannula includes a restriction end having a restriction end diameter, the restriction end diameter greater than a diameter of a nasal vestibule of the nasal passageway to prevent the cannula from passing completely through the nasal passageway.

10. An apparatus according to claim 7, wherein the cannula has a length approximately equivalent to a distance between a nasal vestibule of the nasal passageway and an epiglottis of the patient.

11. An apparatus according to claim 7, further comprising a second nasal applicator coupled to the support frame, the second nasal applicator operable to guide an insertion end of a second cannula into a second nasal passageway to at least partially insert the second cannula into the breathing passage to support the breathing passage during sleep.

12. A cannula for supporting a breathing passage of a patient, comprising:
    an elongated portion configured to support a breathing passage of the patient during sleep;
    an insertion end configured to be inserted through a nasal applicator of an insertion apparatus and through a nasal passageway of a breathing passage of the patient such that the elongated portion is at least partially disposed within the breathing passage;
    a restriction end having a restriction end diameter, the restriction end diameter being greater than a diameter of a nasal vestibule of the nasal passageway to prevent the cannula from passing completely through the nasal passageway; and
    a guiding shaft configured to be disposed within the cannula for directing the insertion end of the cannula through the nasal passageway.

13. A cannula according to claim 12 wherein the cannula has a length approximately equivalent to a distance between a nasal vestibule of the nasal passageway and an epiglottis of the patient.

14. A method for inserting a cannula for supporting a patient's breathing passage, and for removing the cannula, comprising:

for each of a plurality of treatment sessions, performing an insertion and removal process including:
removably coupling a support frame of an insertion apparatus to a patient to position a nasal applicator proximate to a nasal passageway of a breathing passage of the patient;
guiding an insertion end of a cannula through the nasal applicator and through the nasal passageway such that the cannula is at least partially inserted into the breathing passage for supporting the breathing passage during sleep, wherein guiding the insertion end of a cannula through the nasal applicator comprises movably advancing the insertion end of a cannula relative to the nasal applicator; and
removing the cannula from the breathing passage by movably retracting the insertion end of the cannula relative to the nasal applicator.

15. A method according to claim 14, further comprising guiding the insertion end into the nasal passageway using a guiding shaft configured to be disposed within the cannula.

16. A method according to claim 14, wherein:
the support frame includes:
a nasal portion operable to support the nasal applicator; and
one or more coupling portions coupled to the nasal portion; and
the method further comprises removably coupling the one or more coupling portions of the support frame to the patient to position the nasal applicator proximate to the nasal passageway.

17. A nasal applicator for use with a system for supporting a patient's breathing passage, the nasal applicator configured to be removably coupled to a support frame configured to position the nasal applicator proximate to a nasal passageway of a patient's breathing passage, the nasal applicator fitting within the nasal passageway and including a curved portion configured to guide a cannula into the nasal passageway during advancement of the cannula relative to the nasal applicator for at least partially inserting the cannula into the breathing passage, and during retraction of the cannula relative to the nasal applicator for removing the cannula from the breathing passage after each at least partial insertion of the cannula into the breathing passage, said cannula having a cross section sufficient to support the breathing passage during sleep.

18. A system for supporting a breathing passage of a patient, comprising:
means for supporting a breathing passage of a patient, the support means configured to be inserted through a nasal passageway of the breathing passage to at least partially insert the means for supporting the breathing passage into the breathing passage; and
insertion means for inserting the means for supporting the breathing passage into the breathing passage, the insertion means including:
nasal application means operable to guide the means for supporting the breathing passage through the nasal application means and into the nasal passageway, wherein the nasal application means fits within the nasal passageway and includes a curve configured to guide the means for supporting the breathing passage within the nasal passageway; and
patient interfacing means for positioning the nasal application means proximate to the nasal passageway, the patient interfacing means configured to be releasably coupled to the patient to position the nasal applicator proximate to the nasal passageway, wherein the patient interfacing means includes:
a nasal portion operable to support the nasal application means; and
one or more coupling portions operable to removably couple the nasal portion to the patient to position the nasal application means proximate to the nasal passageway.

19. A system for supporting a breathing passage of a patient, comprising:
a cannula configured to be at least partially inserted into a breathing passage of a patient, the cannula comprising:
an insertion end configured to be inserted through a nasal passageway of the breathing passage; and
a cross-section sufficient to support the breathing passage during sleep;
wherein the cannula includes a restriction end having a restriction end diameter, the restriction end diameter greater than a diameter of a nasal vestibule of the nasal passageway to prevent the cannula from passing completely through the nasal passageway; and
an insertion apparatus including:
a nasal applicator operable to guide the cannula through the nasal applicator and into the nasal passageway; and
a support frame coupled to the nasal applicator, the support frame configured to be releasably coupled to the patient to position the nasal applicator proximate to the nasal passageway, wherein the support frame includes:
a nasal portion operable to support the nasal applicator; and
one or more coupling portions operable to removably couple the nasal portion to the patient to position the nasal applicator proximate to the nasal passageway.

20. An insertion apparatus for use with a system for supporting a patient's breathing passage, comprising:
a nasal applicator operable to guide an insertion end of a cannula into a nasal passageway of a patient's breathing passage to at least partially insert the cannula into the breathing passage, the cannula having a cross-section sufficient to support the breathing passage during sleep, and the cannula including a restriction end having a restriction end diameter, the restriction end diameter greater than a diameter of a nasal vestibule of the nasal passageway to prevent the cannula from passing completely through the nasal passageway; and
a support frame coupled to the nasal applicator, the support frame configured to be releasably coupled to the patient to position the nasal applicator proximate to the nasal passageway, wherein the support frame includes:
a nasal portion operable to support the nasal applicator; and
one or more coupling portions operable to removably couple the nasal portion to the patient to position the nasal applicator proximate to the nasal passageway.

21. A nasal applicator for use with a system for supporting a patient's breathing passage, the nasal applicator configured to be removably coupled to a support frame configured to position the nasal applicator proximate to a nasal passageway of a patient's breathing passage, the nasal applicator further configured to guide a cannula into the nasal passageway during advancement of the cannula relative to the nasal applicator for at least partially inserting the cannula into the breathing passage, and during retraction of the cannula relative to the nasal applicator for removing the cannula from the breathing passage after each at least partial insertion of the cannula into the breathing passage, the cannula having a cross section sufficient to support the breathing passage during sleep, and the cannula including a restriction end having a restriction end diameter, the restriction end diameter greater than a diameter of a nasal vestibule of the nasal passageway to prevent the cannula from passing completely through the nasal passageway.

22. A system for supporting a breathing passage of a patient, comprising:

means for supporting a breathing passage of a patient, the support means configured to be inserted through a nasal passageway of the breathing passage to at least partially insert the means for supporting the breathing passage into the breathing passage, the means for supporting the breathing passage including means for preventing the entire means for supporting the breathing passage to pass through a nasal vestibule of the nasal passageway; and insertion means for inserting the means for supporting the breathing passage into the breathing passage, the insertion means including:

nasal application means operable to guide the means for supporting the breathing passage through the nasal application means and into the nasal passageway, wherein the nasal application means fits within the nasal passageway and includes a curve configured to guide the means for supporting the breathing passage within the nasal passageway; and patient interfacing means for positioning the nasal application means proximate to the nasal passageway, the patient interfacing means configured to be releasably coupled to the patient to position the nasal applicator proximate to the nasal passageway, wherein the patient interfacing means includes:

a nasal portion operable to support the nasal application means; and one or more coupling portions operable to removably couple the nasal portion to the patient to position the nasal application means proximate to the nasal passageway.

23. An insertion apparatus for use with a system for supporting a patient's breathing passage, comprising:

a nasal applicator operable to guide an insertion end of a cannula into a nasal passageway of a patient's breathing passage to at least partially insert the cannula into the breathing passage, the cannula having a cross-section sufficient to support the breathing passage during sleep;

a guiding shaft configured to be disposed within the cannula for directing the insertion end of the cannula through the nasal passageway; and a support frame coupled to the nasal applicator, the support frame configured to be releasably coupled to the patient to position the nasal applicator proximate to the nasal passageway.

\* \* \* \* \*